(12) United States Patent
Benezri (10) Patent No.: US 11,918,543 B2
(45) Date of Patent: Mar. 5, 2024

(54) PLUSH TOY WITH SENSORY DEVELOPMENT

(71) Applicant: Lulyboo, LLC, Lake Forest, CA (US)

(72) Inventor: Pazit Benezri, Irvine, CA (US)

( * ) Notice: Subject to any disclaimer, the term of this patent is extended or adjusted under 35 U.S.C. 154(b) by 93 days.

(21) Appl. No.: 17/229,769

(22) Filed: Apr. 13, 2021

(65) Prior Publication Data

US 2022/0323305 A1    Oct. 13, 2022

(51) Int. Cl.
| | | |
|---|---|---|
| *A63H 3/02* | (2006.01) | |
| *A61J 17/00* | (2006.01) | |
| *A61J 17/02* | (2006.01) | |
| *A61M 21/02* | (2006.01) | |
| *A63H 3/00* | (2006.01) | |
| *A63H 3/28* | (2006.01) | |
| *A61M 21/00* | (2006.01) | |

(52) U.S. Cl.
CPC ............ *A61J 17/1111* (2020.05); *A61J 17/02* (2013.01); *A61M 21/02* (2013.01); *A63H 3/003* (2013.01); *A63H 3/02* (2013.01); *A63H 3/28* (2013.01); *A61M 2021/0011* (2013.01); *A61M 2021/0027* (2013.01); *A61M 2021/0061* (2013.01); *A63H 3/001* (2013.01)

(58) Field of Classification Search
CPC .......... A63H 3/00; A63H 3/003; A63H 3/005; A63H 3/006; A63H 3/02; A63H 3/28; A63H 3/36; A63H 33/00; A63H 33/004; A61J 17/00; A61J 17/001; A61J 17/10; A61J 17/101; A61J 17/1011; A61J 17/111; A61J 17/1111
USPC ...... 446/72, 73, 81, 227, 297, 369; 606/234, 606/235
See application file for complete search history.

(56) References Cited

U.S. PATENT DOCUMENTS 3,955,314 A * 5/1976 Robb .................. A61J 17/1111
446/72
4,204,362 A * 5/1980 Fournier ................. A61J 17/02
446/73

(Continued)

FOREIGN PATENT DOCUMENTS

DE        29921951 U1    3/2000
WO     2009038519 A1    3/2009

OTHER PUBLICATIONS www.shumee.in/products/baby-bunny-teether-and-rattle-plushtoy 4 pages; Printed: Mar. 25, 2021.

(Continued)

*Primary Examiner* — Alexander R Niconovich
(74) *Attorney, Agent, or Firm* — Rimas T. Lukas (57) ABSTRACT

The plush toy includes a head attached to a body having two leg-like appendages. The toy has an opening leading to a first pocket located inside the body. The first pocket is interconnected to a second pocket located inside the head. The opening to the second pocket at the intersection of the head and body can be closed with a hook-and-look type fastener. The second pocket contains a sensory stimulus module capable of playing music, vibrating, and emitting white noise at different volumes to sooth a child. When inserted inside the second pocket, buttons on the module are aligned with indicia on the posterior side of the head which permit a user to press through the fabric to activate and control the module. A teether in the shape of hugging arms is attached to the toy and provides teething relief and enjoyment for the child.

14 Claims, 9 Drawing Sheets

(56) References Cited

U.S. PATENT DOCUMENTS

| | | | | | |
|---|---|---|---|---|---|
| 4,277,910 | A | * | 7/1981 | Kramer | A63H 3/003 446/73 |
| 4,505,687 | A | * | 3/1985 | Munro | A63H 3/02 446/385 |
| 5,312,282 | A | * | 5/1994 | Cooper | A61J 9/00 215/11.1 |
| 5,344,355 | A | * | 9/1994 | Silverstein | A61J 17/1111 446/72 |
| 5,385,573 | A | * | 1/1995 | Wright | A63H 3/003 446/28 |
| 5,993,285 | A | * | 11/1999 | Sofia | A63H 3/14 446/26 |
| 6,343,968 | B1 | | 2/2002 | Louie | A47G 9/083 5/413 R |
| 6,461,214 | B1 | * | 10/2002 | Lynch | A61J 17/001 446/73 |
| 6,638,133 | B1 | * | 10/2003 | Brancolino | A63H 3/52 446/385 |
| 6,666,740 | B1 | * | 12/2003 | Schneider | A61J 17/1111 446/72 |
| 6,827,317 | B1 | * | 12/2004 | Maki Risaliti | A61J 17/02 248/105 |
| 7,244,166 | B1 | * | 7/2007 | Sherman | A63H 3/02 446/369 |
| 10,052,264 | B2 | * | 8/2018 | McClintock | A63H 3/003 |
| 10,058,486 | B2 | * | 8/2018 | Steward | A61J 17/02 |
| 10,172,394 | B2 | * | 1/2019 | Hyslop | A45F 5/02 |
| 10,258,544 | B2 | * | 4/2019 | Kim | A61J 17/001 |
| 11,141,668 | B2 | * | 10/2021 | Lakritz | A63H 3/02 |
| 2004/0116040 | A1 | * | 6/2004 | Mulvihill | A63H 33/00 446/247 |
| 2005/0245968 | A1 | * | 11/2005 | Huberman | A61J 17/1111 606/235 |
| 2008/0305711 | A1 | * | 12/2008 | Kazakoff | A63H 3/02 446/369 |
| 2009/0030455 | A1 | * | 1/2009 | Dallman | A61J 17/1111 606/236 |
| 2009/0081921 | A1 | * | 3/2009 | Urueta | A61J 17/113 606/236 |
| 2009/0270010 | A1 | * | 10/2009 | Scott | A61J 17/1111 446/72 |
| 2010/0304636 | A1 | * | 12/2010 | Seiz | A63H 3/02 446/72 |
| 2010/0317252 | A1 | * | 12/2010 | Raimondi | A63H 3/02 446/73 |
| 2012/0041487 | A1 | * | 2/2012 | Griffis | A45F 5/02 606/234 |
| 2015/0004872 | A1 | * | 1/2015 | Taylor | A61J 17/111 446/227 |
| 2015/0004873 | A1 | * | 1/2015 | Schecter | A63H 3/36 446/376 |
| 2015/0112121 | A1 | * | 4/2015 | Eyrun | A63H 3/28 600/28 |
| 2016/0158112 | A1 | * | 6/2016 | Summers | A63H 3/02 446/73 |
| 2016/0236103 | A1 | * | 8/2016 | Pettrey, III | A63H 3/02 |
| 2016/0296847 | A1 | * | 10/2016 | Joo | A63H 33/006 |
| 2017/0028304 | A1 | * | 2/2017 | Stray | A63H 3/005 |
| 2017/0151504 | A1 | * | 6/2017 | Villano | A61J 17/02 |
| 2018/0001222 | A1 | * | 1/2018 | Guebenlian | A63H 3/02 |
| 2018/0078866 | A1 | * | 3/2018 | Rogone | A61J 17/1111 |
| 2018/0161685 | A1 | * | 6/2018 | Garren | G09B 19/00 |
| 2019/0175454 | A1 | * | 6/2019 | Pierce | A61J 17/1111 |
| 2020/0152074 | A1 | * | 5/2020 | Henley | H04R 1/028 |
| 2022/0031999 | A1 | * | 2/2022 | Gmelig | A61M 21/02 |
| 2022/0054796 | A1 | * | 2/2022 | McGreevy | A61M 21/02 |

OTHER PUBLICATIONS www.etsy.com/in-en/listing/895900822/personalized-baby-teether-baby?ga_order=most_relevant&ga_search_type=all&ga_view_type=gallery&ga_search_query=plush+teether&ref=sr_gallery-1-9&organic_search_click=1 13 pages; Printed: Mar. 25, 2021.

www.etsy.com/in-en/listing/912581894/baby-teether-wooden-crochet-rattle-toy?ga_order=most_relevant&ga_search_type=all&ga_view_type=gallery&ga_search_query=plush+teether&ref=sr_gallery-1-49&organic_search_click=1&pro=1&frs=1 8 pages; Printed: Mar. 25, 2021.

* cited by examiner

PLUSH TOY WITH SENSORY DEVELOPMENT

FIELD OF THE INVENTION

This application relates generally to toys, and in particular, to a plush toys incorporating sensory development features for children.

BACKGROUND OF THE INVENTION

Sensory and motor development in infants is a gradual process by which a child gains use of muscles and begins to experience new awareness through sight, touch, taste, smell and hearing. Balance and movement improve as an infant gains use and coordination of muscles. During this time a child may reach toward an object and grasp at toys with their hands using their palms. With time, babies develop more control over their hands and fingers and may be able to grab different sized objects with their forefinger and thumb. Visual sensory development includes focusing on an object and following a toy or other object with increasing distance. Hearing develops and babies are amused and comforted by various sounds. The sense of touch becomes well developed with the child preferring soft, gentle touches and cuddles. Also, babies like to experience and explore objects through taste and texture which prompts them to put almost anything they can into their mouths. Especially when teething, a hard object helps the child cope with pain and provide relief. There is a need to promote a variety of sensory development in a child including motor and tactile skills, grasping, manipulation, touch and hearing while providing soothing relief and comfort to the touch and teeth. The present invention addresses these needs by providing a plush toy having a variety of sensory development features.

SUMMARY OF THE INVENTION

According to one aspect of the invention, a plush toy having a body with an elongate shape and two leg-like appendages extending toward a distal end is provided. The body of the toy includes an inner body cavity having a body opening. The toy includes a head connected to the body. The head includes an inner head cavity that is interconnected to the inner body cavity via a head opening. The toy includes a teether having a first end and a second end connected to the body. The teether is curved between the first end and the second end defining a semi-circular shape and a crescent-like opening between the body and the teether. The toy includes a removable stimulus generator located inside the head cavity.

According to another aspect of the invention, a toy is provided having a body made entirely of fabric material including a first layer as an exterior layer and a second layer as an interior layer. The body has an elongate shape and is bifurcated at a longitudinal axis into two leg-like appendages extending to a distal end. The body has an inner body pocket defined by the interior layer. The body pocket has a proximal opening facing a proximal end and a distal-facing body opening between the two appendages. The toy includes a head having an outer layer and an inner layer with batting material filled between the outer layer and the inner layer. The inner layer defines a head pocket having a distal-facing head opening. The head is connected to the body such that the first layer and second layer of the body are attached directly to the head such that both the first layer and second layer encompass head opening. The body pocket is interconnected with the head pocket via the proximal opening and the head opening. The toy includes a teether having two spaced-apart proximal ends connected to an anterior side of the body. The teether defines a crescent-shaped opening between the teether and body. The teether has a curved semi-circular shape.

According to another aspect of the invention, a method for attaching a plush toy to an elongated object is provided. The method includes the step of providing a toy. The toy includes a teether having a first end and a second end. The teether is curved between the first end and the second end and defines a semi-circular shape. The toy includes a body made entirely of fabric material. The body includes a first leg extending to a first distal end and a second leg extending to a second distal end. The toy includes a head connected to the body. The head includes an inner head cavity that is interconnected to the inner body cavity via a head opening. The toy includes a teether having a first end and a second end connected to an anterior side of the body and defining an opening between the teether and body. The teether has a curved semi-circular shape, a front side and a back side. The method includes the step of placing an elongated object between the teether and the body. The method includes the step of moving the first leg around the elongated object such that the elongated object is between the body and the first leg. The method includes the step of passing the first distal end and at least part of the first leg through the opening from under the back side of the teether to the front side of the teether. The method includes the step of moving the second leg around the elongated object such that the elongated object is between the body and the second leg. The method includes the step of passing the second distal end and at least part of the second leg through the opening from under the back side of the teether to the front side of the teether.

DETAILED DESCRIPTION OF THE INVENTION

Turning now to FIGS. 1-7, the present invention will now be described in detail. A plush toy 10, which may also be referred to herein as a doll 10, having sensory development features is provided. The toy includes a head 12 connected to a body 14 that is connected to a teether 16, and a removable sensory stimulus generator 18 inside the toy 10.

The head 12 includes an outer surface made of soft, plush fabric material and an inner surface made of soft, plush, fabric material with soft batting material, such as cotton, polyester, wool or the like, sandwiched therebetween. The inner surface of fabric material is configured to form an internal head pocket (not shown) having a caudal-facing head opening (not shown) interconnecting the head pocket to an interior of the body 14. The head pocket is sized and configured to receive the removable stimulus generator 18 which is insertable into the head pocket through the head pocket opening. The stimulus generator 18 is secured within the head pocket by its conforming size and the size of pocket opening. The head pocket opening is provided with fastener, such as a hook-and-loop type fastener, at the intersection of the head pocket and interior of the body 14 so that the stimulus generator does not slide, rotate or otherwise move or migrate from its intended orientation with respect to the head 12.

Figures 6, 7:
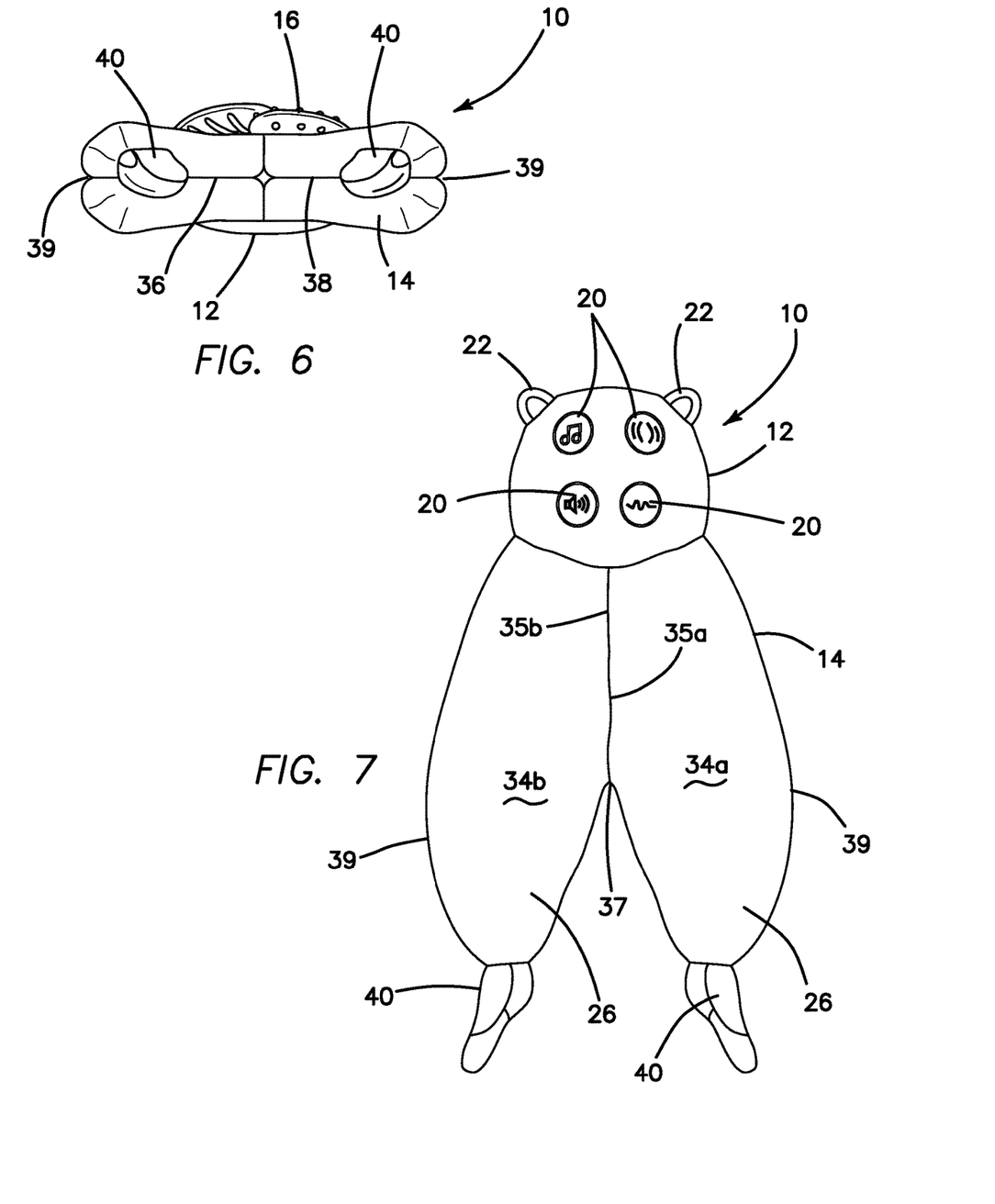
FIG. 6 is a bottom plan view of a plush toy according to the present invention.
FIG. 7 is a rear plan view of a plush toy according to the present invention.

The posterior facing portion of the outer surface of the head 12 includes markings or indicia 20 stitched into the fabric material. The indicia 20 are preferably symbols representing music, vibration, volume and white noise that correspond to control features on the stimulus generator 18 located inside the head 12 The indicia 20 are sized and configured so that a user can press in the location of the indicia 20 and press through the fabric layers to select the indicated control features such as buttons on the stimulus generator 18. The stimulus generator 18 and its use will be described in greater detail below.

Figures 1, 2:
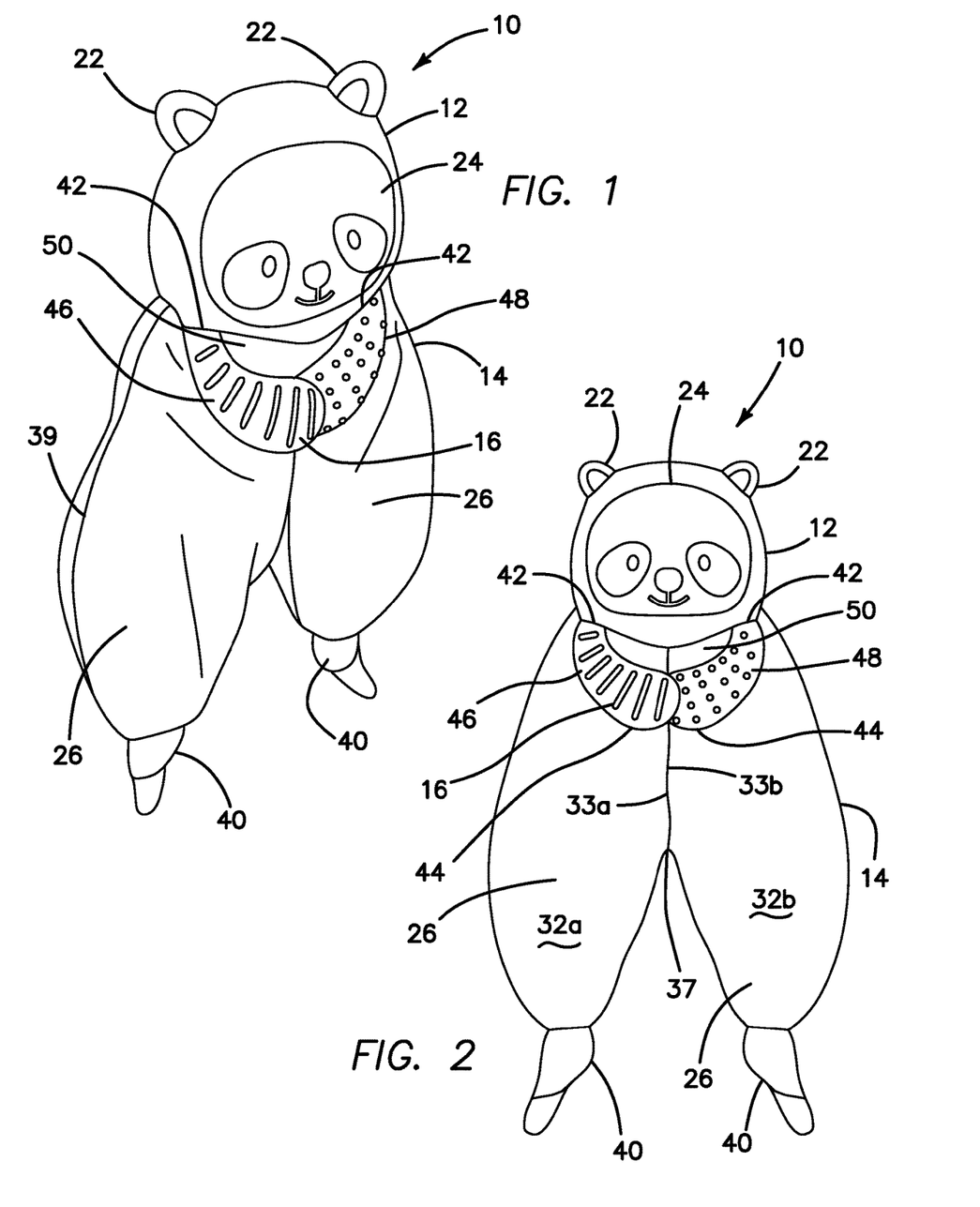
FIG. 1 is a top perspective view of a plush toy according to the present invention.
FIG. 2 is a front plan view of a plush toy according to the present invention.

The top of head 12 includes two ears 22 protruding from the head 12. The ears 22 are configured to comport with the shape and size of an animal, animal-like, humanoid, cartoon character or other creature that the plush toy/stuffed animal 10 is intended to convey. The anterior facing portion of the outer surface of the head 12 includes a face 24 stitched or sewn into the fabric material. The face 24 includes a perimeter, which may have a rounded or other shape, at least one eye, nose and mouth. The facial features are sized and configured to correspond with the intended animal, animal-like, humanoid, cartoon or other creature the toy 10 is intended to simulate. For example, a panda is being simulated in the toy 10 shown in the figures. The panda is shown to have characteristic elongated-shaped outlines around the eyes which may be black in color against a white-colored face.

The elongate body 14 has a proximal or cephalad end that is connected to the head 12. The body 14 is bifurcated into two leg-like appendages 26 beginning approximately midway along the longitudinal length of the body 14 and extend toward the distal end. The body 14 defines an inner body pocket 28 having a proximal opening (not shown) that is interconnected with the head opening at the proximal end, thereby, placing the head pocket in communication with the body pocket 28. The head opening opens into the body pocket/cavity 28. The body pocket 28 also has a generally caudal-facing body opening 30 located between the two appendages 26. The body 14 generally forms a tubular shape with an interior body pocket 28 extending between a proximal opening at the head 12 and a distal body opening 30 between the legs 26. The body 14 is formed by an outer surface made of soft, plush, fabric material connected to an inner surface made of soft, plush, fabric material with soft batting material, such as cotton, polyester, wool or the like, filled therebetween with the inner surface layer defining the interior body pocket 28.

In one variation, the anterior outer surface is comprised of two elongated and tapered anterior fabric panels 32a, 32b that are connected together along an upper portion of their respective medial edges 33a, 33b proximal to the point/line of bifurcation 37. The posterior outer surface is comprised of two elongated and tapered posterior fabric panels 34a, 34b that are identical in size and shape to the anterior panels 32a, 32b and connected together along an upper portion of their respective medial edges 35a, 35b proximal to the point of bifurcation. The lateral edges 39 of the anterior panels 32a, 32b are connected to the lateral edges 39 of the posterior panels 34a, 34b and the top edges of the anterior panels 32a, 32b and posterior panels 34a, 34b are connected to the head 12 encompassing the head opening forming the proximal opening of the body 14. The inner surface layer of the body 14 is formed by a first or left inner fabric panel 36 connected to an identical second or right inner fabric panel 38. Each of the first and second inner panels 36, 38 is wider at the proximal end and tapers toward the distal end. Each inner panel 36, 38 is about equal in size to one outer anterior panel 32a, 32b combined with one outer posterior panel 34a, 34b, respectively. The first inner panel 36 is curved or folded about itself such that the portions of its lateral outer edges that are cephalad to the point of bifurcation are aligned at the midline. The second inner panel 38 is also curved or folded about itself such that the portions of its lateral outer edges that are proximal to the point of bifurcation are also aligned at the midline and connected, such as by sewing, to the portion of aligned lateral edges of the first inner panel 36 that are proximal to the point of bifurcation. The lateral edge of the first inner panel 36 that is anterior and distal to bifurcation 37 is connected to the medial edge 33a of the outer anterior panel 32a and the lateral edge of the first inner panel 36 that is posterior and distal to the point of bifurcation 37 is connected to the medial edge 35a of the outer posterior panel 34a. Similarly, the lateral edge of the second inner panel 38 that is anterior and distal to the point/line of bifurcation 37 is connected to the medial edge 33b of the outer anterior panel 32b and the lateral edge of the second inner panel 38 that is posterior and distal to the point of bifurcation is connected to the medial edge 35a of the outer posterior panel 34a. The tapering fabric material constituting the leg-like distal appendages 26 advantageously permits the tips 40 of the appendages 26 to be tied into a simple knot such as an overhand knot so that the tips 40 resemble little feet.

Since the interior body pocket or cavity 28 is defined by the inner fabric layer(s) it has an amorphous shape that is delimited by boundaries that are stitched to the outer fabric layer(s). As such, the interior body pocket 28 is confined by the outer fabric layer(s) but free to move and be folded with respect to the outer fabric layer(s) because there is space between the inner fabric layer(s). The outer fabric layer(s) confine the inner fabric layer(s) at stitched edge borders along the body and along the appendages 26. The body pocket 28 is defined by at least two folds of inner fabric material. The body pocket 28 extends from the first leg-like appendage to the second leg-like appendage and is approximately equal to or slightly smaller than the width of the torso of the body and approximately equal or slightly smaller in length than the longitudinal length of the torso of the body. The body cavity 28 is sized such that a child's hand can be placed inside the pocket 28 and the child can play with the toy 10 and manipulate the toy 10 like a puppet. Also, a child can put things into the body pocket and/or head pocket and use the pockets to hide candy or other objects.

Figure 3:
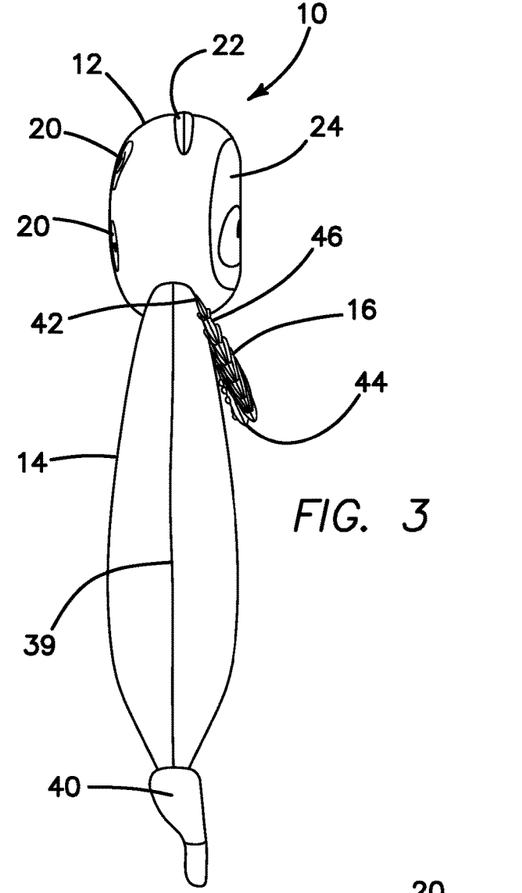
FIG. 3 is a right-side plan view of a plush toy according to the present invention.
Figure 4:
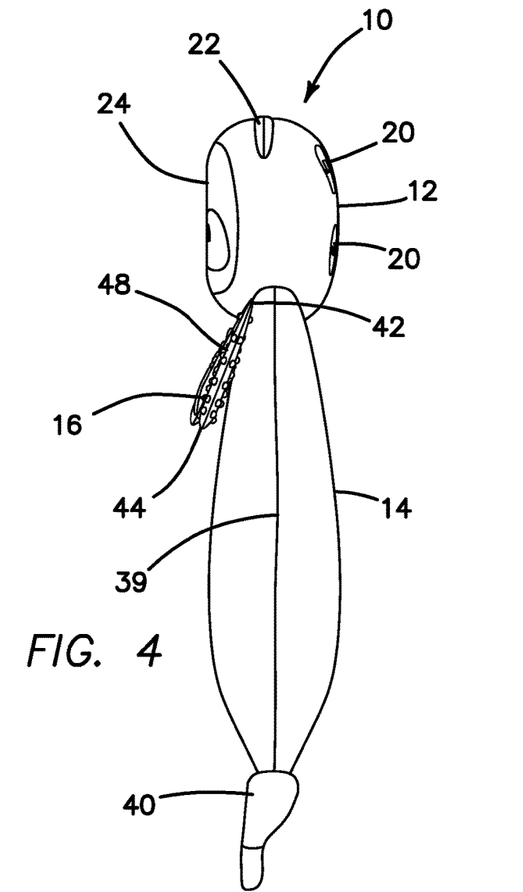
FIG. 4 is a left-side plan view of a plush toy according to the present invention.
Figure 5:
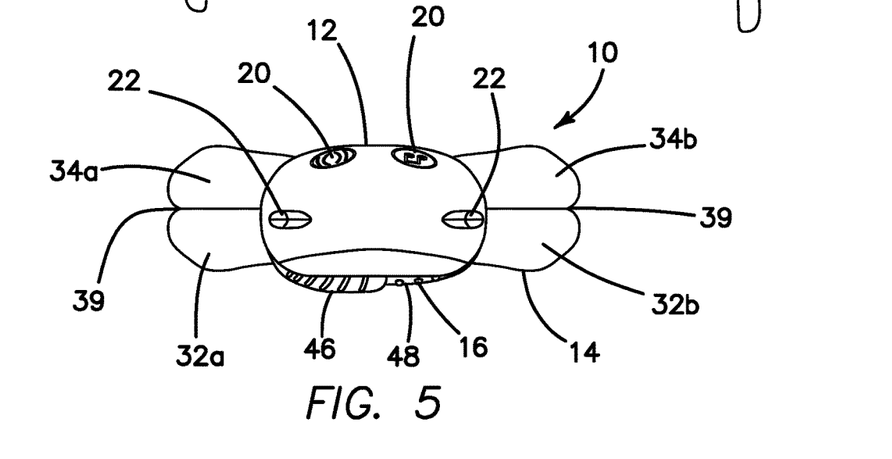
FIG. 5 is a top plan view of a plush toy according to the present invention.

The teether 16 is attached to the front of the toy 10. The teether 16 has two proximal ends 42. The two proximal ends 42 are free and laterally spaced apart, disconnected, disjointed from each other. These free ends 42 are connected to the body 14, in particular, at the intersection of the head 12 and body 14. The proximal ends 40 of the teether 16 are provided with holes (not shown) so that thread can be used to securely attach the teether 16 by sewing from the inside so that the securement is not visible. Best seen from a front plan view such as FIG. 2, the teether 16 has a width that is smaller at the two proximal ends 42 and increases in width at the distal ends 44. The teether 16 is configured to resemble arms and hands joined together in hugging-like fashion. As such the teether 16 has a right arm 46 and a left arm 48 joined together and molded as a unitary object such that the arms 46, 48 are not separable at the hands. Hence, the arms 46, 48 constitute the teether 16 itself. Each arm 46, 48 extend from the body and are joined at their distal ends or hands. The proximal ends are not joined together. The teether 16 is molded from a single piece of suitable teething material such as child safe plastic, silicone or rubber that is firm yet slightly resilient. The material of the teether 16 is non-toxic, non-allergenic, elastomeric and non-nutritive suitable for teething and sucking. The teether 16 is easily cleaned and designed not to harbor infectious germs. The right arm 46 is configured to overlap the left arm 48 so that the distal end of the right arm 46 or hand is on top of the distal end of the left arm 48. The thickness of the teether 16 also increases from the proximal ends 42 to the distal ends 44 as can be seen in FIGS. 3-4. This variation in thickness of the teether 16 advantageously provides a range of thickness for the child to bite on while offering resistance to biting teeth. Furthermore, the right arm 46 is provided with a raised textured pattern that is different from the raised textured pattern on the left arm 48. In particular, the raised textured pattern on the obverse side of the right arm 46 comprises a plurality of spaced apart raised, parallel lines and is the same on the reverse side; whereas, the raised textured pattern on the obverse side of left arm 48 comprises a plurality of rows of raised dots and is the same on the reverse side as can be seen in FIG. 6. This variable texture advantageously fosters sensory development by giving the child a variety of textures to feel and bite into. The embossed pattern on each arm 46, 48 is aligned on the obverse and reverse sides encouraging the child to play and to angulate the teether 16 in a variety of ways child allowing to experiment with and explore different positions of the teether between the teeth or fingers that is most soothing or entertaining. The teether 16 is curved and crescent-shaped defining a crescent-shaped opening between the arms 46, 48 and head 12 and body 14. The entirety of the teether 16 does not form a complete circle but is curved and semi-circular. The teether 16 generally extends, hangs downwardly/distally from the head 12; however, the teether 16 is not ridgedly fixed to the head 12 or body 14 and is capable of movement such as flipping up and down relative to the head 12 and/or body 14. Since the arms 46, 48 are fixedly attached to each other and non-separable, the toy 10 advantageously displays a permanent hugging appearance and, when raised into a flipped-up position, a joyous affection is conveyed. The crescent-like opening 50 provides an opening for the child to pass other objects through whether it be a finger or hand. The teether 16 in combination with the opening 50 gives the child a location to grasp and hold the toy 10 to carry it around. If the child grasps the teether 16 near the proximal ends 42 of the teether 16, the thickness and width of the teether 16 will be smaller facility grasping for smaller hands relative to grabbing the teether at its distal end where it is thicker, thereby, advantageously providing sensory development opportunities should the child grasp the thicker and wider distal ends 44 of the teether 16 relative to the thinner and narrower proximal ends. Further advantages of the teether 16 as it relates to attachment of the toy 10 to elongated objects will described below.

Figure 8:
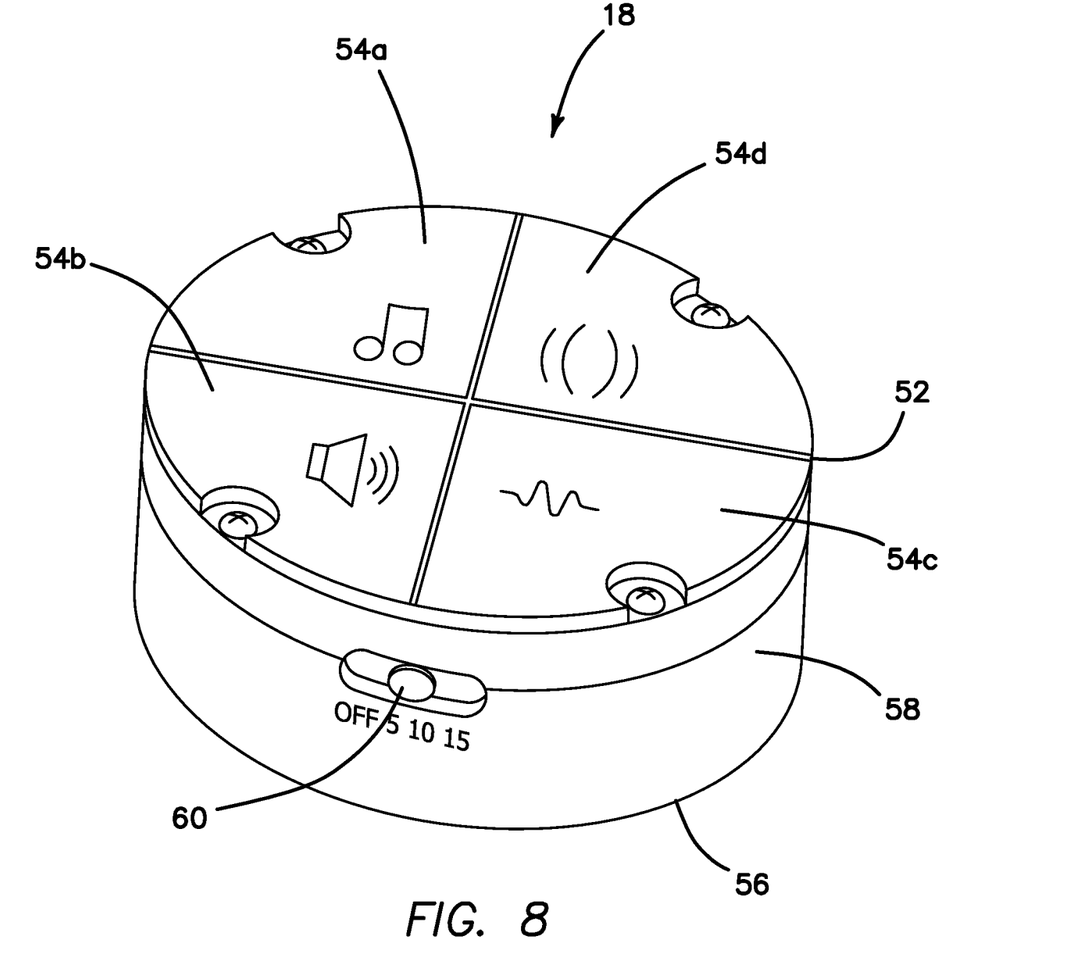
FIG. 8 is a top perspective view of a stimulus generator according to the present invention.

Turning now to FIG. 8, the sensory stimulus generator module, or box 18 will now be described in greater detail. The module 18 is cylindrical in shape having a posterior face 52 bearing a plurality of buttons 54. The posterior face 52 is parallel to and opposite from an anterior face 56. The posterior face 52 and anterior face 56 are interconnected by a sidewall 58 giving a module a puck-like shape. The module 18 includes a power supply such as replaceable or rechargeable batteries, a microprocessor, memory, at least one speaker, vibrator, and power switch interconnected and configured to provide a variety of modes of operation generating different types of stimulus for a child that are selectable by the user via the buttons on the posterior face 54. The power switch 60 is located on the caudal side of the sidewall 58. The power switch 60 is in the form of a slider switch having four positions: POWER OFF, 5 MINUTES, 10 MINUTES AND 15 MINUTES. Moving the slider from the OFF position turns the module on for a pre-set duration selectable for 5, 10 or 15 minutes of activation based on the position of the switch 58. After the pre-set duration of activation, the activation stops. The switch 58 is large enough to provide the user with a tactile sensation through the fabric of the toy 10 so that not only the switch 58 can be located through the fabric but also moved between the positions of 5, 10 and 15 minutes and the positions easily identified without looking at the module 18. The switch 60 is located on the caudal side in order to advantageously provide the user with a means of orientating the module 18 prior to insertion into the toy 10 such that the four buttons 54 on the posterior face 52 of the module 18 are aligned with the corresponding indicia 20 on the posterior side of the head 12. The four buttons 54 comprise four distinct quadrants on the posterior face 52 with the four buttons 54 filling up the entire posterior surface 52 to advantageously give the user a large surface area in which to depress and successfully activate a button without directly observing the module 18.

The four buttons 54 correspond to the four modes of operation of the stimulus generator 18. One button 54a bearing a symbol comprising music notes is for activating a melody. Different types of music may be stored in the memory of the module 18. The module 18 is configured so that each button can be pressed multiple times in sequence to select different options of a particular mode of operation. To select the melody mode of operation, the button 54a with music notes is depressed once to play classical music such as Brahms or Mozart and the like. When the same button 54a is pressed twice in sequence, a children's tune such as "Rock-A-Bye Baby" a is played. When the same button 54a is pressed three times in sequence, the melody is switched to play a different children's tune such as "Twinkle Twinkle Little Star". Hence, the melody mode allows the user to select between different types of music, melodies, children's songs, nursery rhymes and the like. When the same button 54a is depressed four times, the melody mode is turned off. Another mode of operation is volume adjustment. Depressing the volume button 54b once increases the volume to a high setting. When the volume button 54b is pressed twice the volume is decreased to a low setting. The default volume setting is medium volume which is the volume setting when the melody mode button 54a is pressed. The symbol for the volume button 54b is a picture of a speaker. The same symbol that is on the button 54b is also stitched on the posterior surface of the head 12. The module 18 also includes a white noise mode of operation which is activated by pressing the button 54c bearing a horizontal wavy line. This symbol is also stitched in a corresponding location on the posterior surface of the head 12. One press of the white noise button 54c causes the module to play the sound of a human heartbeat. Pressing the same button 54c twice in sequence causes the module to play the sound of a mother's womb. Pressing the same button 54c three times causes the module to play sounds of ocean waves. Pressing the white noise button 54c four times, turns off the white noise mode of operation. Another mode of operation for the module 18 is vibration mode which is activated by depressing a button 54d have a symbol of double parentheses one time. Depressing the vibration mode button 54d twice turns off the vibration. After the vibration button 54d is pressed a once, pressing the same button 54d once will cause the vibration level to cycle through gentle, medium, and strong vibration levels. The vibration mode can be used in combination with the melody mode or white noise mode which will continue to play if selected before during or after vibration mode is selected. In another variation, the module 18 includes an input such as a USB cable jack or short-range wireless for uploading music, white noise and vibration files or for connecting to an application loaded on a portable cellular device for controlling the module 18. The module 18 provides auditory sensory development for the child by providing a variety of auditory, musical, vibratory stimulus while providing comfort through soothing sounds.

Figure 9:
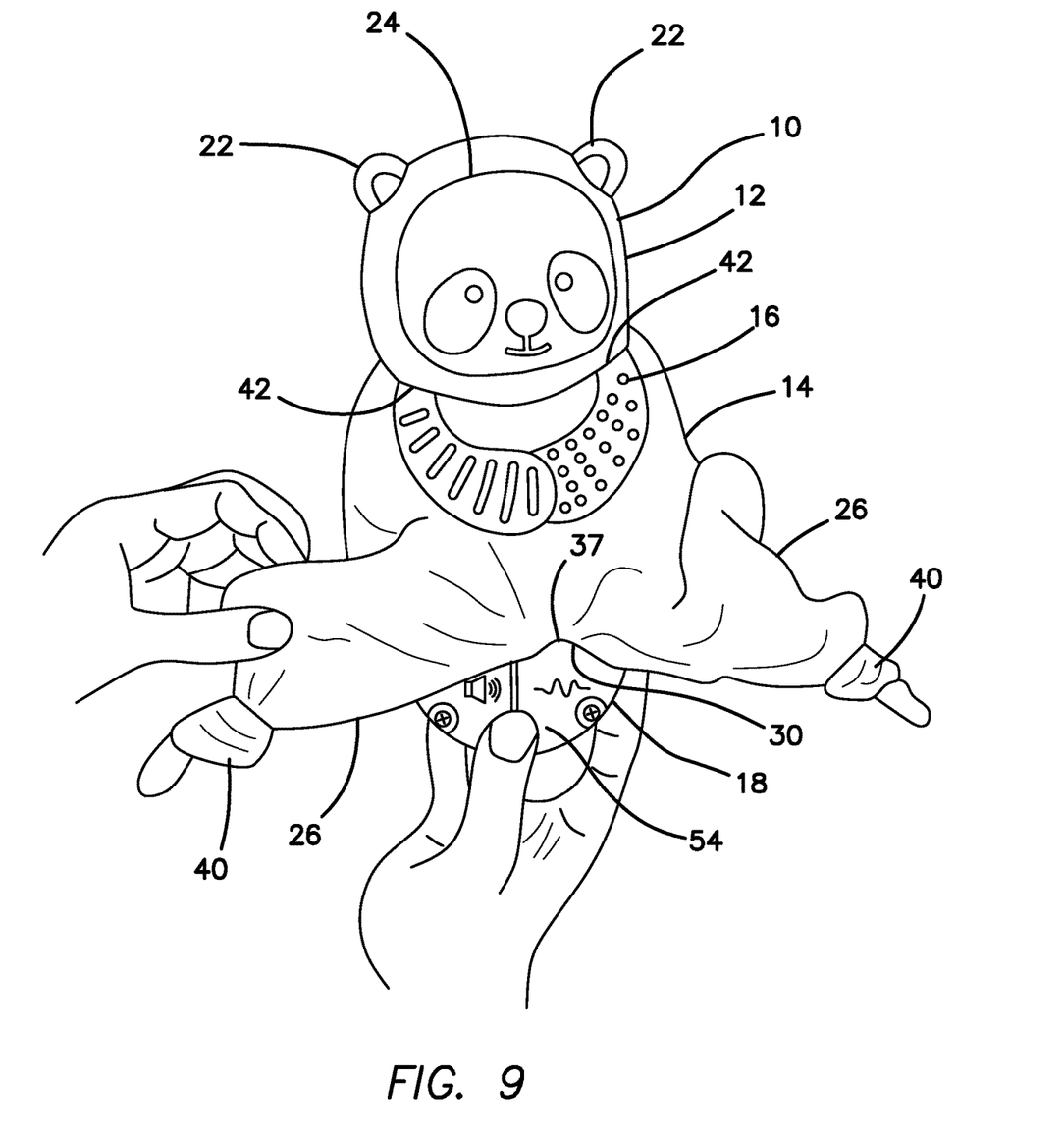
FIG. 9 is a top perspective view of a plush toy illustrating insertion of a stimulus generator according to the present invention.
Figure 10:
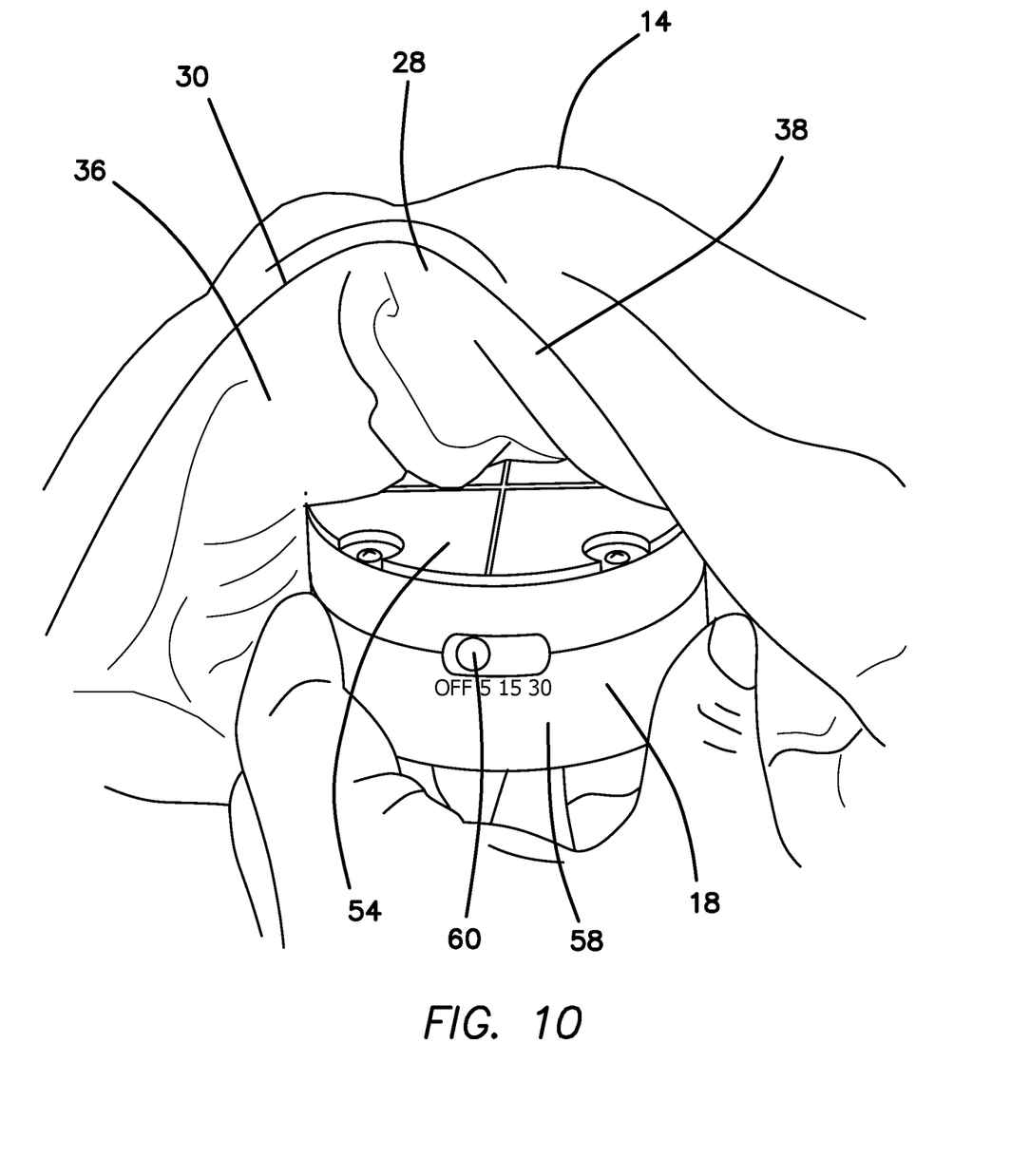
FIG. 10 is a bottom perspective view of a plush toy illustrating insertion of a stimulus generator according to the present invention.

Turning now to FIGS. 9-10, the module 18 is shown being inserted into the body pocket 28 of the toy 10. The module 18 is first orientated such that the buttons 54 face the posterior side of the toy 10 and the switch 60 is position in the caudal direction of the toy 10. The module 18 is then inserted into the body opening 30 and into the body pocket 28 along a midline approach from the bifurcation point 37 between the appendages 26. From the body pocket 28, the module 18 is further passed through the proximal opening of the body 14 and further through the head opening and into the head pocket of the head 12. The body pocket 28 is larger than the head pocket. Once inserted into the head pocket, the internal fastener at the head opening can be closed. If the fastener is a hook-and-loop type fastener, the two sides of the hook and loop fabric are brought together to close the head pocket and, thereby, prevent the module from migrating out of the head pocket. The head pocket is sized and configured to closely conform to the size and shape of the module 18. As a result of the head pocket conforming to the module 18 and due to the proper orientation of the module upon insertion, the four buttons 54 on the posterior face 52 of the module 18 will be positioned to correspond to the indicia 20 on the outer posterior surface of the head 10 such that, for example, pressing in the location of the indicia 20 having a music note symbol will result in the pressing of the melody button 54a on the module. The fabric is of sufficient thickness to permit pressing through the outer fabric layers of the head 12 to reach the module buttons 54 and power switch 60.

Figure 11:
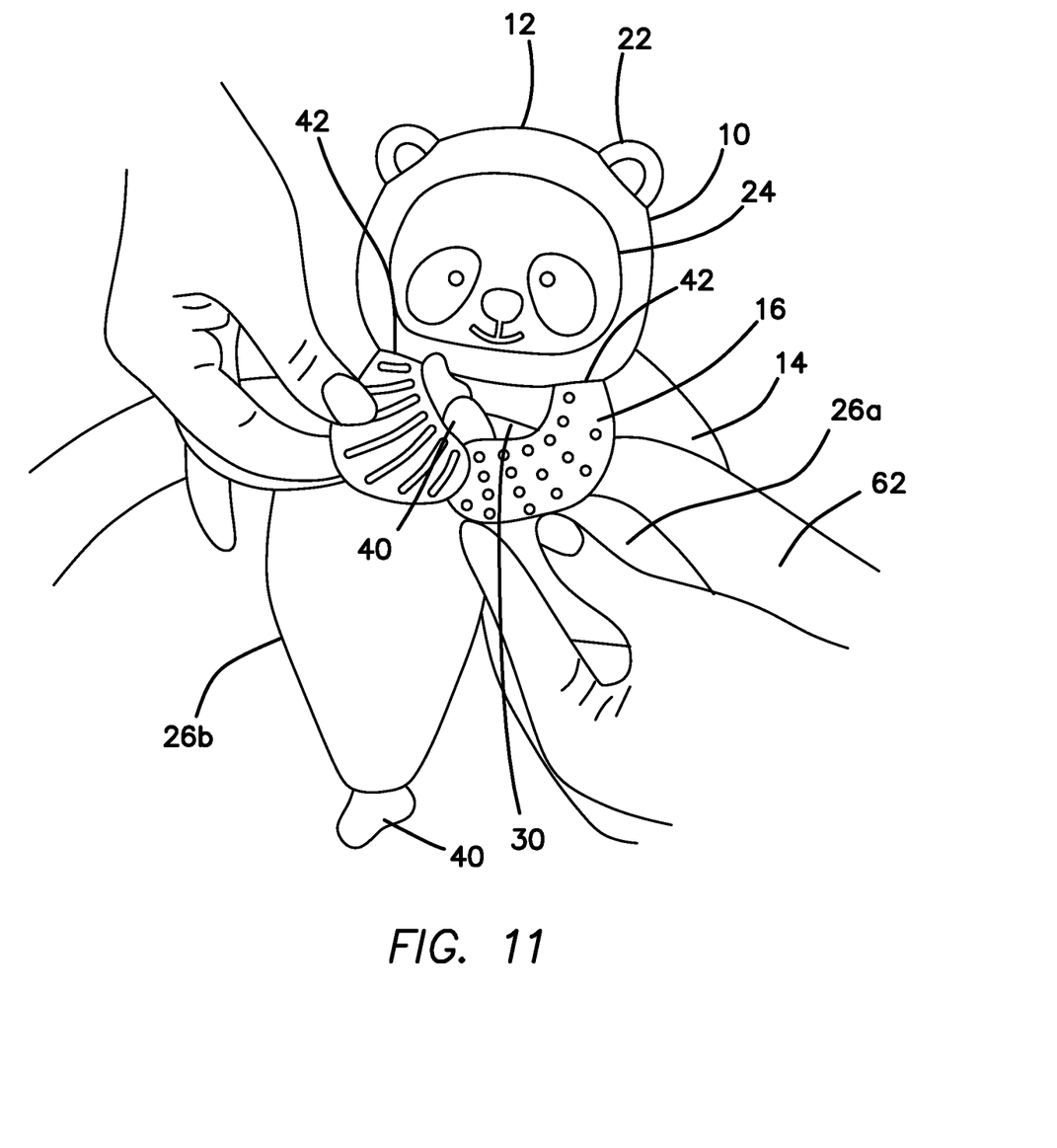
FIG. 11 is a top perspective view of a plush toy illustrating attachment of a first limb of the plush toy to an object according to the present invention.
Figure 12:
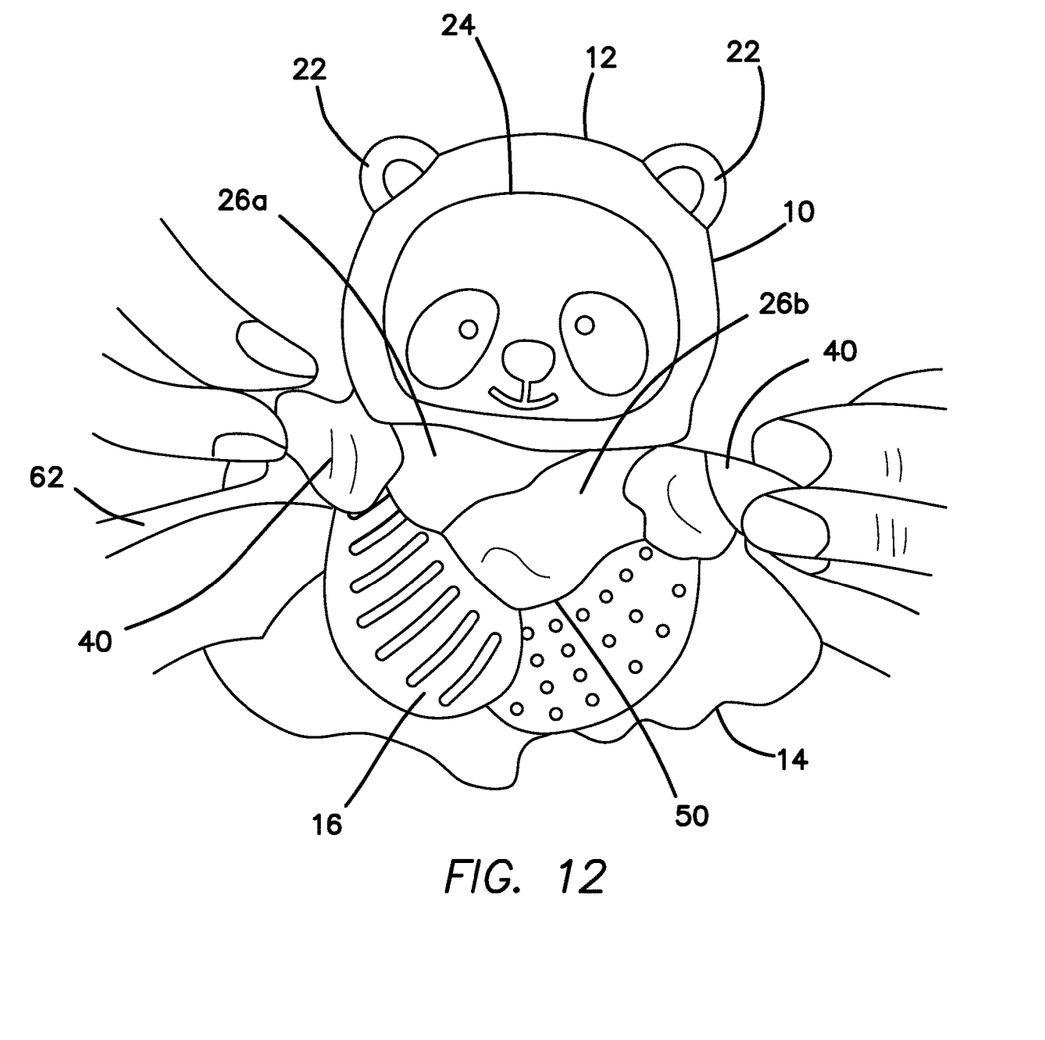
FIG. 12 is a top perspective view of a plush toy illustrating attachment of a first limb and a second limb of the plush toy to an object according to the present invention.
Figure 13:
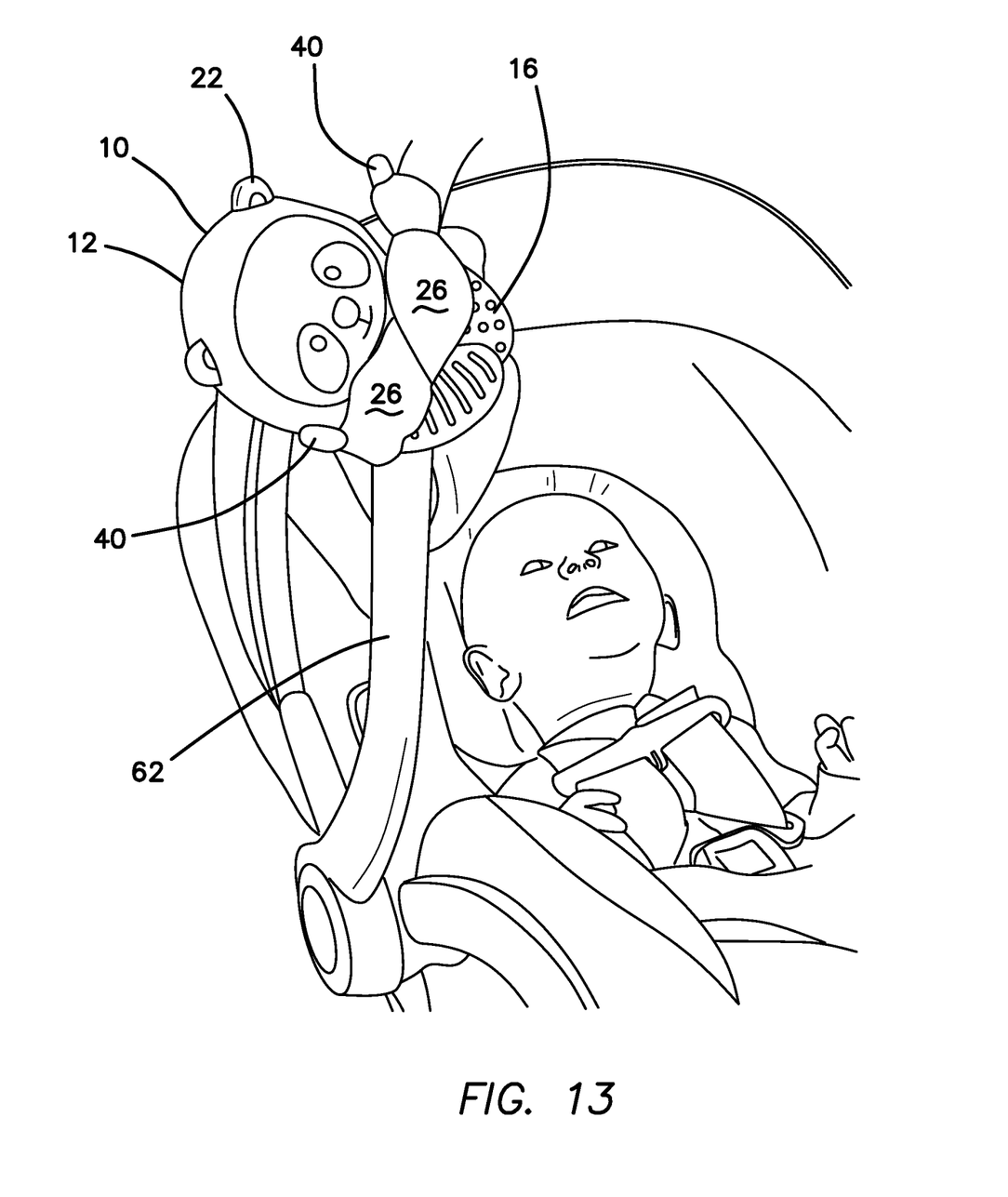
FIG. 13 is a top perspective view of a plush toy attached to a baby stroller according to the present invention.

Turning now to FIGS. 11-13, attachment of the toy 10 to an object will now be described. The body 14 of the toy 10 is soft and flexible and the appendages 26 can be easily folded, moved, manipulated and even tied together. The body 14 together with the teether 16 provide the user with a unique way of attaching the toy 10 to an object. The toy 10 may be attached to a variety of objects within the vicinity of a child. Such objects include but are not limited to elongate objects such as handles of a stroller, railing of a baby bed, hanging stands, bars and the like. The teether 16 is moved upwardly from a downwardly depending position and is placed atop or hooked on an object targeted for attachment. In the figures, the target object is a round, cylindrical bar 62 of a baby stroller. The teether 16 is placed such that its reverse or backside side of the teether 16 makes contact with the bar 62; thereby, the teether 16 is placed on the bar 62. Because the teether 16 is heavy, the toy 10 is capable of being balanced on the bar with the teether 16 being placed on the bar and the body 14 of the toy 10 hanging down one side of the bar 62. Because the teether 62 resembles arms, the plush doll 10 gives the appearance of holding or hanging on to the bar 62. To further secure the toy 10 to the bar 62, one of the appendages 26, the left leg 26a, is grasped by the user and moved around the bottom of the bar 62, wrapping at least partially around it and up through the crescent-shaped opening 50 formed by the teether 16 as shown in FIG. 11. The legs may be passed from the backside of the teether 16 through the opening 50 toward the front side. Also, in another variation, the legs may be passed from the frontside of the teether 16 through the opening 50 toward the backside. FIG. 11 shows the tips 40 of the appendages being tied with knots to form feet-like ends. The left leg 26a can be pulled through the crescent opening 50 to tighten the strength of the attachment. Then the other one of the two appendages 26, the right leg 26b is grasped by the user and moved around the bottom of the bar 62 and up through the crescent-shaped opening 50 formed by the teether 16 as shown in FIG. 12. The appendages 26 are passed through the opening 50 in a criss-cross manner from the posterior direction toward the anterior direction to emerge in front of the doll 10 and, in another variation, from the anterior direction toward the posterior direction to emerge from behind the teether 16. The left leg 26a and or the right leg 26b can be pulled in either direction through the crescent-shaped opening 50 to tighten or loosen the strength of the attachment. A toy attached to the stroller bar 62 is shown in FIG. 13. The toy 10 provides a cute and cuddly appearance with its legs 26a, 26b passed through the teether 16 giving the appearance of it sitting with its legs crossed and entertaining the child from a different location. When attached, the child can reach for the toy 10, grab it, rotate it around the bar 62, detach and re-attached the toy as desired.

It is understood that various modifications may be made to the embodiments of the plush toy disclosed herein. Therefore, the above description should not be construed as limiting, but merely as exemplifications of preferred embodiments. Those skilled in the art will envision other modifications within the scope and spirit of the present disclosure.

I claim:
1. A toy comprising:
   a body having an elongate shape and two leg-like appendages extending to a distal end; the body including an inner body cavity having a body opening;

a head connected to the body; the head including an inner head cavity that is interconnected to the inner body cavity via a head opening; and a teether having a first end and a second end each connected directly to the body;

the teether being curved between the first end and the second end defining a semi-circular shape.

2. The toy of claim 1 further including a removable stimulus generator located inside the head cavity.

3. The toy of claim 2 wherein the stimulus generator is insertable and removable from the head cavity through the head opening via the body cavity and through the body opening.

4. The toy of claim 2 wherein the stimulus generator is configured to generate music, white noise and vibration.

5. The toy of claim 2 wherein the stimulus generator includes an arrangement of buttons on one face of the stimulus generator.

6. The toy of claim 5 wherein an outer surface of a backside of the head includes indicia having an arrangement that aligns and corresponds to the arrangement of buttons on the stimulus generator.

7. The toy of claim 1 wherein the teether increases in thickness from the first and second ends.

8. The toy of claim 1 further including an internal fastener configured to close the head opening.

9. The toy of claim 1 wherein the body opening opens to an exterior of the body.

10. A toy comprising:
a body made entirely of fabric material including a first layer as an exterior layer and a second layer as an interior layer; the body having an elongate shape and being bifurcated at a longitudinal axis into two leg appendages extending to a distal end; the body having an inner body pocket defined by the interior layer; the body pocket having a proximal opening facing a proximal end and a distal-facing body opening between the two leg appendages;

a head connected to the body; the head having an outer layer and an inner layer with batting material filled between the outer layer and the inner layer; the inner layer defining a head pocket having a distal-facing head opening; the head being connected to the body such that the first layer and second layer of the body are attached directly to the head such that both the first layer and second layer encompass the head opening and the body pocket is interconnected with the head pocket via the proximal opening and the head opening;

a teether having two spaced-apart proximal ends connected to an anterior side of the body and defining a crescent-shaped opening between the teether and body; the teether having a curved semi-circular shape.

11. The toy of claim 10 further including soft batting material located between the first layer and second layer.

12. The toy of claim 10 wherein the teether increases in thickness and width with distance from the two proximal ends.

13. The toy of claim 10 wherein the teether is defined by a first arm appendage and a second arm appendage joined together.

14. The toy of claim 13 wherein the teether has a first raised textured pattern on the first arm appendage and a second raised textured pattern that is different from the first pattern on the second arm appendage.

* * * * *